United States Patent [19]

Lowe

[11] Patent Number: Plant 6,961

[45] Date of Patent: Aug. 1, 1989

[54] VARIEGATED EVERGREEN AZALEA PLANT

[76] Inventor: Hubert G. Lowe, Rte. 1, Box 21, Elon, N.C. 27244

[21] Appl. No.: 56,986

[22] Filed: Jun. 3, 1987

[51] Int. Cl.[4] ..... A01H 5/00

[52] U.S. Cl. ..... Plt./55

[58] Field of Search ..... Plt./57, 55

*Primary Examiner*—Robert E. Bagwill

*Attorney, Agent, or Firm*—C. Robert Rhodes; Judith E. Garmon

[57] ABSTRACT

An azalea plant having variegated leaves and deep red blossoms.

1 Drawing Sheet

The present invention is a new and distinct evergreen azalea which has a deep red bloom and variegated foliage. The new azalea is the issue of an asexually propagated bud sport taken from the parent azalea plant Sunglow.

The sport was discovered by the inventor in a cultivated block of Sunglow azaleas at Lowe Nursery, Inc. in Elon College, N.C. in approximately July, 1985.

After discovery of the sport, soft wood cuttings were taken and the new variety was propagated, with resulting consistency in asexual reproduction. The rooted cuttings formed parent stock and the variety has been asexually reproduced through approximately four generation at the time of filing. One hundred percent rootability and consistently variegated foliage has been demonstrated.

Hardiness was tested in zones five and six; (Zones of Hardiness U.S.D.A. Map) and it is believed that the new variety is hardy at temperatures to −5° F. (5 degrees below 0 Fahrenheit). Under properly maintained conditions, it is believed the new azalea will demonstrate minimal damage during the winter season.

The proposed variety name for the new azalea plant is Red Lustre.

The accompanying pictorial illustration is a mass of blooms and variegated foliage in natural color, reproduced according to state-of-the-art technological processes to achieve maximum accuracy of color reproduction.

DETAILED DESCRIPTION OF THE PLANT

The color references shown in parentheses in the following detailed description are to The Royal Horticultural Society Colour Chart, Revised Edition, 1986.

Foliage: The leaves are, at maturity, one inch to two inches in length and approximately one-half inch to one inch in width. The shape is lanceolate to oblanceolate with an acuminate tip. Color ranges from a medium green (138B) in the spring to a deeper, lustrous green (138A) in the summer, with a cool white (155A) margin of approximately one-sixteenth inch to one-fourth inch substantially surrounding each leaf. The mature branches are brown (200D) and new leaf stems are a yellow-green (151A).

Flowers: The flowers are quite large, having a mature width of three inches to three and one-half inches, with a length of two and one-fourth inches to two and one-half inches. Flowers are borne in clusters of three, with the clusters measuring approximately six inches in width. The flowers have four petals, with smooth edges, and a substantively elliptic to ovate shape. There are four stamens, curved, and approximately one inch to one-fourth inch long. The pistil is approximately two inches long and curved.

Flower color is a deep purple red (60B) with darker red shading (60A). The stamens are deep reddish pink (60D). The pistil is deep reddish pink (60D) with a darker red (60A) stigma. The closed bud is dark red (60A).

Growth habit is upright to broad, of medium size, very floriferous.

What is claimed is:

1. A new and distinct variegated, evergreen azalea plant substantially as herein shown and described; characterized by a unique purple-red bloom and lustrous green foliage with white margins.

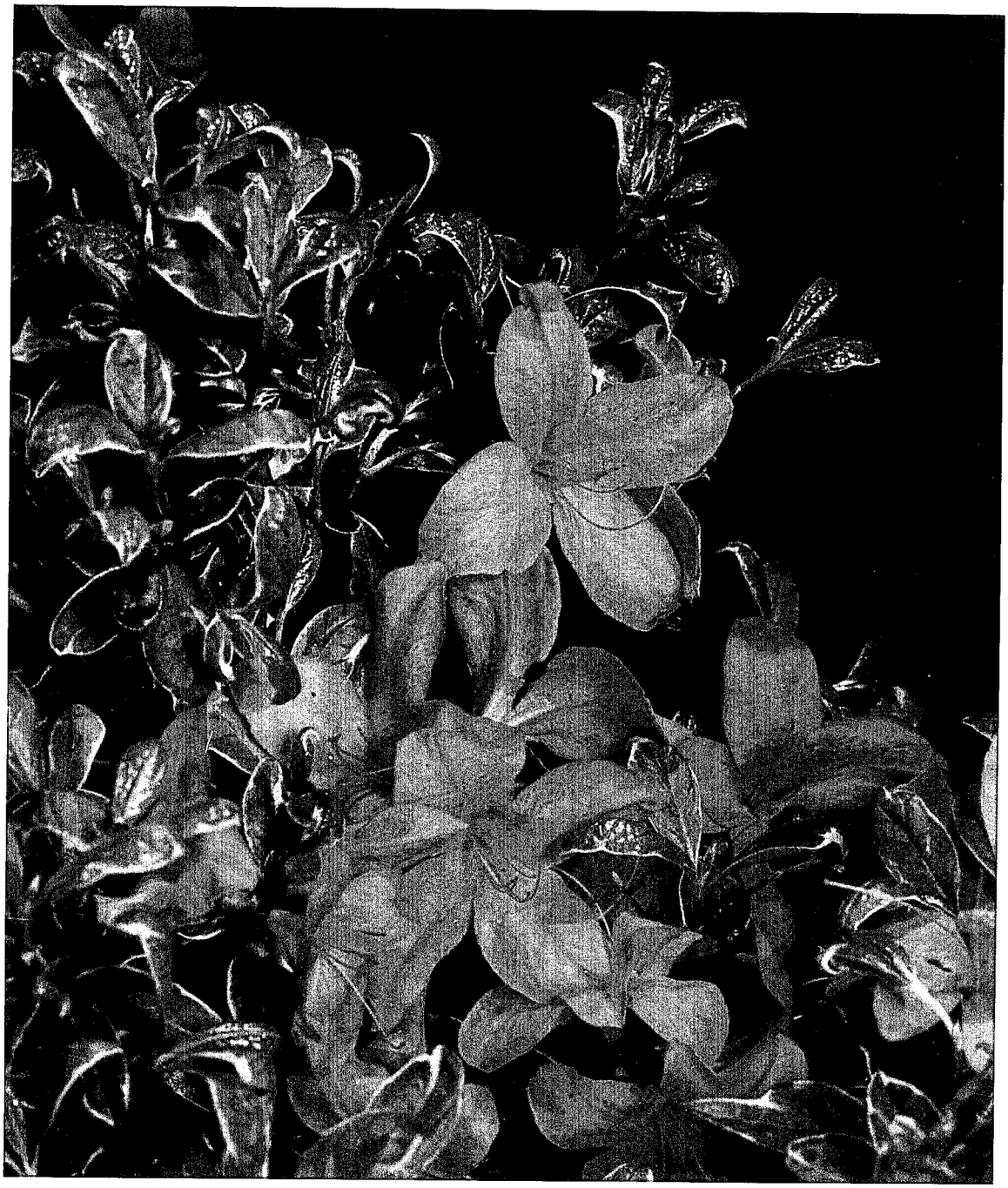

* * * * *